(12) United States Patent
Jung et al.

(10) Patent No.: US 11,033,695 B2
(45) Date of Patent: Jun. 15, 2021

(54) METERED DOSE INHALER

(71) Applicant: Presspart GmbH & Co. KG, Marsberg (DE)

(72) Inventors: Benjamin Jung, Cologne (DE); Matthias Seiler, Düsseldorf (DE); Till Von Den Driesch, Erkelenz (DE)

(73) Assignee: Presspart GmbH & Co. KG, Marsberg (DE)

( * ) Notice: Subject to any disclaimer, the term of this patent is extended or adjusted under 35 U.S.C. 154(b) by 322 days.

(21) Appl. No.: 15/896,501

(22) Filed: Feb. 14, 2018

(65) Prior Publication Data
US 2018/0236187 A1    Aug. 23, 2018

(30) Foreign Application Priority Data
Feb. 20, 2017    (EP) .................................... 17156995

(51) Int. Cl.
*A61M 15/00*    (2006.01)

(52) U.S. Cl.
CPC ........ *A61M 15/009* (2013.01); *A61M 15/007* (2014.02); *A61M 15/008* (2014.02); *A61M 15/0091* (2013.01); *A61M 2205/8206* (2013.01)

(58) Field of Classification Search
CPC .. A61M 15/00; A61M 15/007; A61M 15/008; A61M 15/009; A61M 15/0071; A61M 15/0068; A61M 15/0021; A61M 15/0025; A61M 15/0065; A61M 15/02; A61M 11/02; A61M 11/00; A61M 11/06; A61M 11/08

USPC ...... 116/200, 306–308, 317, 318; 377/15–17
See application file for complete search history.

(56) References Cited

U.S. PATENT DOCUMENTS

| | | | | |
|---|---|---|---|---|
| 4,744,495 A | * | 5/1988 | Warby | B65D 83/54 222/402.16 |
| 5,544,647 A | | 8/1996 | Jewett et al. | |
| 6,029,659 A | | 2/2000 | O'Connor | |
| 7,219,664 B2 | * | 5/2007 | Ruckdeschel | A61M 15/0091 128/200.14 |
| 7,819,075 B2 | * | 10/2010 | Bowman | A61M 15/009 116/307 |
| 7,896,001 B2 | * | 3/2011 | Harrison | A61M 15/0091 128/200.14 |
| 9,517,314 B2 | * | 12/2016 | Hately | G06M 1/02 |
| 2004/0255936 A1 | | 12/2004 | Urbanus | |
| 2005/0076904 A1 | * | 4/2005 | Jones | A61M 15/009 128/200.23 |

(Continued)

FOREIGN PATENT DOCUMENTS

DE    102011007008 A1    10/2012
GB    2506385 A    4/2014

(Continued)

*Primary Examiner* — LaToya M Louis
(74) *Attorney, Agent, or Firm* — Nields, Lemack & Frame, LLC

(57) ABSTRACT

The invention relates to a metered dose inhaler (1) for dispensing aerosol doses with an actuation housing (2) and a canister (5) with an aerosol. A triggering unit (8) comprises one single trigger member (21) on a flexible member (22) for activating a switch (19) of a circuit assembly. The flexible member (22) is configured to interact with the canister (5) in such a way that the trigger member (21) is moved in a lateral direction by the canister (5) so that the trigger member (21) engages the switch (19).

15 Claims, 4 Drawing Sheets

(56) References Cited

U.S. PATENT DOCUMENTS

2012/0080029 A1 4/2012 Koerner et al.
2014/0008384 A1 1/2014 Helmlinger

FOREIGN PATENT DOCUMENTS

| WO | 91/06334 A1 | 5/1991 |
| WO | 2005/009325 A2 | 2/2005 |
| WO | 2016/030844 A1 | 3/2016 |

* cited by examiner

METERED DOSE INHALER

TECHNICAL FIELD

The present invention relates to a metered dose inhaler for dispensing aerosol doses comprising an actuation housing and a canister containing an aerosol and having a valve located at a valve end of the canister. The canister is received in the actuation housing and is configured to move in a longitudinal direction from a rest position to an activation position in which the valve of the canister is depressed against a bottom portion of the actuation housing such that an aerosol dose is released. A triggering unit with a trigger member is configured to interact with the canister when the canister moves in a longitudinal direction from the rest position to the activation position. A circuit assembly has a substrate with a switch thereon, the switch being configured to interact with the trigger member such that the trigger member triggers the switch when the canister moves from the rest position to the activation position.

BACKGROUND OF THE INVENTION

Metered dose inhalers (MDIs) are medication delivery devices that are often used to deliver a pharmaceutical formulation including one or more pharmaceutically active compounds to a human or other mammalian patient. The MDI device currently in use is comprised of an L-shaped dispenser housing (usually plastic) and an aerosol canister (metal). The aerosol canister contains medication and is capable of delivering a finite number of metered doses of medication. The aerosol canister is inserted into the L-shaped dispenser housing in inverted orientation. The bottom of the canister is facing upward and the canister's valve end is facing downward. The patient self-administers the medication.

Typically, the pharmaceutical formulation is delivered by the MDIs in unit doses in the form of an aerosol. Each actuation of the MDI delivers one unit dose. The unit dose is expelled by the MDI and is taken into the body of the patient upon inhalation, via the nose or mouth. The pharmaceutical formulation is then delivered to the lungs of the patient. Metered dose inhalers are typically used for the treatment of respiratory infections and disorders including respiratory tract infections, obstructive lung disease, inflammatory lung disease and chronic obstructive pulmonary disease. Asthma treatment is a particularly commonly use of MDIs.

In the field of MDIs, it is desired to provide reliable and cost-effective products. In the recent years, efforts have been made to provide MDIs with dose counters and additional functions such as monitoring functions or evaluation functions. Based on these additional functions the physician or patient may for example monitor the frequency of dispensed doses and the point of time when these doses have been dispensed. While these additional functions are beneficial in terms of the products reliability, the integration of advanced functions is regularly connected with increasing production costs.

WO 2016/030844 A1 describes a metered dose inhaler with an actuation housing in which two separate trigger members are actuated by the canister in two different longitudinal positions of the canister. The first trigger member is actuated upon displacement of the canister from the rest position to a first longitudinal position, thereby indicating that the user intends to dispense a dose of the aerosol. The canister is then moved from the first longitudinal position to a second longitudinal position in which the valve is opened and the aerosol is dispensed. When the aerosol is dispensed, the second trigger member is actuated. The arrangement of two trigger members distributed at different positions along the axis of displacement of the canister avoids incorrect interpretation of switch signals when the dose inhaler falls on the ground. While the provision of two trigger members enhances the reliability of the device, the production of the dose inhaler is comparatively costly.

U.S. Pat. No. 6,029,659 A describes an inhalation device with a counter located at the lower end of the device. The counter includes a rod-like push button that is pressed by the canister when the canister is moved into the activation position. The counter is incremented when the push button is depressed in the activation direction into the counter. This occurs when the aerosol canister is depressed to release medication. It cannot be excluded that wear effects such as deformation or material fatigue of the push button affect the actuation of the counter when the canister is displaced so that the position in which the canister releases the aerosol is not matched with the position in which the counter is actuated. Further, because the actuation force is directly induced into the rod-like push button in the axial direction of the rod structure, the axial load on the push button may result in deformations of the same so that the functional reliability cannot be ensured. In the worst case, the dispense of the aerosol is not captured by the counter mean at all. Moreover, the assembly of the inhalation device is comparatively complicated because the push button is located close to the predetermined pathway of the aerosol so that only a restricted space is available for installing the counting mechanism.

SUMMARY OF THE INVENTION

It is object of the invention to provide for a cost effective and highly reliable metered dose inhaler.

The above-mentioned object is achieved by a metered dose inhaler comprising the features of claim 1 and a triggering unit comprising the features of claim 14. Preferred embodiments are set up in the dependent claims.

According to the present invention, the triggering unit comprises only one single trigger member. The trigger member is provided on a flexible member of the triggering unit or is formed by a flexible member of the triggering unit. The flexible member is configured to interact with the canister, respectively to be engaged by the canister, and to be moved in a lateral direction that is transverse to the longitudinal direction in which the canister is moved in the housing from the rest position to the activation position. The circuit assembly has a substrate with a switch thereon, wherein the switch is configured to interact with the trigger member in such a way that the trigger member triggers the switch when the canister moves from the rest position to the activation position. The flexible member is arranged such that after a predetermined displacement of the canister from the rest position into an intermediate position the canister interacts with the flexible member so that the trigger member on the flexible member triggers the switch when the canister reaches the intermediate position. Displacement of the canister from the intermediate position to the activation position then causes displacement of the valve so that an aerosol dose is released. Alternatively, the flexible member is arranged such that the trigger member triggers the switch when the canister reaches the activation position.

In the sense of the invention, the term 'trigger member' is to be understood in a functional way as means to engage the switch. Thus, the trigger member may be provided on a flexible member, e.g. the trigger member may be provided on the flexible member by a structure attached to or formed integrally with the flexible member, or the trigger member may be formed by a flexible member, e.g. by a flexible member having a portion or section assigned to engage the switch. The trigger member may be of any suitable shape for engaging the switch. For example, the trigger member may include a knob or a projection on the flexible member.

In the sense of the invention, the term 'flexible member' relates to a 'moveable/displaceable element' of the triggering unit, wherein this moveable/displaceable element or a part of this moveable/displaceable element is configured to be moved laterally by the canister. Consequently, the term 'flexible member' may include various implementations that are adapted for engaging the canister such as to be moved laterally so that the trigger member triggers the switch. In particular, the term 'flexible member' may include resilient (elastic) elements. Such a 'flexible member' may be elastically deformed or elastically deflected, e.g. by being bent, upon engagement by the canister so that at least a part or section of the flexible member is moved laterally. The term 'flexible member' may also include elements that are not deformed when being engaged by the canister but that are merely displaced. A possible embodiment of a flexible member of this kind is a pivotably mounted member, e.g. a non-resilient member that is attached to a body of the triggering unit by means of a flexible pivot bearing and that is caused to pivot about the bearing point by engagement of the canister. Another embodiment of a flexible member of this kind may be an element that is displaced by the canister in a pure axial motion, e.g. a member that is laterally guided in the actuation housing. In this case, the member and/or the canister may have an inclined engagement surface fur mutual engagement so that the longitudinal movement of the canister is transferred into a lateral displacement of said member.

The movement of the canister in longitudinal directions takes place along a longitudinal axis. The intermediate position is located along the longitudinal axis of the actuation movement between the rest position and the activation position of the canister. The arrival of the canister at the intermediate position may be indicated by the respective arrangement of the flexible member. When the canister arrives at the intermediate position, the canister deflects the flexible member such that the trigger member triggers the switch. Further displacement of the canister from the intermediate position is necessary to dispense the aerosol dose. The trigger member is moveable from a first position to a second position relative to the switch to activate the switch when the canister moves in the longitudinal direction. When the canister engages the flexible member and moves in longitudinal direction, the flexible member deflects and the trigger member is moved from the first into the second position such as to activate the switch.

The location of the intermediate position is chosen at a position which effectively prevents unwanted actuation of the switch when dose inhaler falls on the ground, because prior to dispensing the medicament or actuation of the switch, the patient has to displace the canister along a predetermined distance. When the flexible member with the trigger member is arranged such as to activate the switch in the intermediate position of the canister, a reliable indication of the administration of the patient's medication is ensured. From the intermediate position, the displacement of the canister that is necessary to open the valve is comparatively large in contrast to triggering units where the switch is triggered when the valve is open. The displacement of the canister for finally opening the valve compensates wear effects in the triggering unit such as a reduction of elasticity in the triggering unit's component. Thereby, the reliability of the dose inhaler is ensured. The arrangement of the trigger member in the intermediate position of the canister enables the use of a single trigger member instead of a plurality of trigger members while preserving a high degree of reliability so that so that a further trigger member can be waived. This comes along with a substantial reduction of the production costs. Further, the lateral displacement of the flexible member and the trigger member prevents that the actuation forces acting in the longitudinal direction are directly induced into the switch. Instead, the actuation forces are deflected in lateral direction for switch actuation so that the loads on the triggering unit are reduced. The same accounts when the flexible member with the trigger member is arranged such as to activate the switch in the activation position of the canister where the valve is opened.

According to a further embodiment of the invention, the metered dose inhaler comprises a mechanical dose counter 50 that is arranged such as to be triggered by the canister when the canister moves into the activation position. Mechanical dose counters comprise an indicator member which is constructed and arranged to undergo a predetermined countindicating motion when or before an aerosol dose is released. The mechanical dose counter 50 may be triggered by the canister moving into a dispensing or activation position. A mechanical dose counter is described, for example, in WO 2011/071788 A1. The mechanical dose counter 50 indicates the administering of the medicine by mechanical means. The combination of the triggering unit and the mechanical dose counter 50 and comparison of the electric switch activation and the mechanical dose counting may indicate improper activation of the metered dose inhaler.

According to a yet further embodiment of the invention, when the canister is in the intermediate position, further displacement of the canister toward the activation position triggers opening of the valve so that an aerosol dose is released from the canister.

According to a still further embodiment of the invention, the actuation housing is adapted such that in the intermediate position, the valve of the canister is depressed but closed. This ensures immediate release of the medication and also provides for small displacement necessary to open the valve and dispense the aerosol.

According to a yet further embodiment of the invention, in the intermediate position, the valve of the canister rests against a bottom surface of the actuation housing. Further displacement of the canister is directly transmitted to the valve actuation means, e.g. to a valve stem.

In a further still embodiment of the invention, the triggering unit comprises a body portion that is positioned in the actuation housing between a wall of the actuation housing and the canister, wherein the circuit assembly is attached to the body portion. Preferably, the body portion is formed as one single part.

In a further embodiment of the invention, the body portion is fixed in the actuation housing in the longitudinal direction (vertical fixation). The body portion may be formed as or comprise a plate preferably having a substantially flat main portion and being fixed in the actuation housing such as to extend in longitudinal direction. Preferably, the plate extends substantially parallel to the canister. Also preferably, the plate is fully positioned in the actuation housing between a wall of the actuation housing and the canister. In other words, the plate is received by the actuation housing such that the plate extends in longitudinal direction between a wall of the actuation housing and the canister.

In a still further embodiment of the invention, the flexible member is attached to or formed integrally with the body portion such as to extend from the body portion in longitudinal direction and such as to end in a free end so that the trigger member is resiliently pivotable in the lateral direction with respect to the body portion. Consequently, the flexible member is configured to be moved in lateral direction transverse to the longitudinal direction by the canister by deflection so that the free end of the flexible member moves along a circular-like path such that the trigger member activates the switch when the canister reaches the intermediate position or when the canister reaches the activation position. In other words, the flexible member is a swiveling member that is pivotable with respect to the body portion.

In a further embodiment, the flexible member is primarily tilted or deflected laterally with respect to the body portion when the flexible member is engaged by the canister and moved in lateral direction. In other words, when the flexible member is deflected by the canister, the lateral amount of the shifting movement is larger than the amount of the shifting movement in longitudinal direction. The pivot point of the flexible member may be in the longitudinal direction closer to the rest position than the canister-engaging-end of the flexible member so that the flexible member primarily pivots in lateral direction than in longitudinal direction.

According to a further embodiment, the trigger member is provided on or provided by a flexible tongue that extends at least partially toward the canister. Preferably, the flexible tongue extends from a body portion of the triggering unit in longitudinal direction and a section of the flexible tongue, in particular a free end of the flexible tongue, extends or projects toward the canister. In this regard, the flexible tongue may have a curved of bent shape with a protruding (lower) end projecting toward the canister. For engagement with the canister, the end portion of the flexible tongue may comprise a curved or inclined end face adapted to abut a ferrule of the canister. For stability reasons, the flexible tongue may have a cross-section of rectangular shape at least at the end section thereof.

The switches may be dome-shaped in order to reliably detect triggering of the trigger members.

According to a further embodiment, the actuation housing has a L-shaped hollow body with a dispensing end at one end of the actuation housing and a receiving (installation) end at the other end of the actuation housing, wherein the body portion is mounted in the actuation housing by being inserted into the receiving end. Thereby, the assembly of the metered dose inhaler is simple. The circuit assembly may be attached to the main body portion prior to insertion into the receiving end of the housing. The canister may also be inserted into the receiving end. The dispensing end regularly comprises a mouthpiece for inhalation of the aerosol.

The triggering unit may be positioned within the actuation housing opposite to the mouthpiece. The actuation housing may be adapted to receive the canister in between the triggering unit and the mouthpiece. It is also possible to arrange the triggering unit in between the mouthpiece and the canister.

In a further embodiment, the circuit assembly includes a counting circuit configured to determine the time when the switch is triggered by the trigger member. Determining the holding time the switch is pressed, enables evaluation of the user behavior. The counting circuit may be configured to determine whether the metered dose inhaler is activated when a triggering time of the switch is less than a predetermined threshold value.

According to a further embodiment, the switch is part of an electrical dose counter. For that purpose, the assembly may include a dose counting circuit configured to determine the number of times the switch is triggered by the trigger member.

When the switch is assigned to an electrical dose counter and a counting circuit, various functions can be integrated into the circuit assembly and actuated by a single trigger member. Monitoring functions or evaluation functions for confirming that a patient has taken his medication on a correctly and regular basis can easily be implemented.

Generally, actuation of the switch generates an electrical signal. The electrical signal is processed by the circuit assembly. According to a further embodiment, the metered dose inhaler further comprises a transmitting unit for wirelessly transmitting results processed by the circuit assembly. The results may be transmitted to a user's smartphone or any other electronic device.

In a still further embodiment of the invention, the circuit assembly is provided with additional functions, sensors, such as pressure sensors, or the like, that are activated upon actuation of the switch. The integration of such "wake-up function" helps to save energy. The triggering of the switch triggers the activation of the additional functions that are reactivated from a sleep mode.

According to a further embodiment, biasing means are configured to bias the canister out of the intermediate position toward the rest position. The biasing means act against the actuation direction for dispensing a dose of the aerosol so that the user is forced to overcome a predetermined resistance before he can dispense a dose of the aerosol. This effectively prevents actuation of the switch when the dose inhaler falls on the ground or is accidentally pushed forward.

In a preferred embodiment, the metered dose inhaler comprises a display operatively connected to the circuit assembly and configured to display information processed by the circuit assembly. The information displayed on the display may, for example, include the number of remaining doses left in the canister.

The invention also relates to a triggering unit for a metered dose inhaler for dispensing aerosol, in particular as described herein. Properties and constructive features of the triggering unit described herein in connection with the metered dose inhaler according to the invention also account for the inventive triggering unit and further embodiments thereof.

The respective metered dose inhaler comprises an actuation housing in which a canister containing an aerosol and having a valve located at a valve end thereof is adapted to be received and is configured to move in a longitudinal direction from a rest position via an intermediate position to an activation position, wherein in the activation position the valve is depressed against a bottom portion of the actuation housing such that an aerosol dose is released. Displacement of the canister from the intermediate position to the actuation position causes displacement of the valve so that an aerosol dose is released. The actuation housing houses a circuit assembly having a substrate with a switch thereon.

The triggering unit of the invention comprises a single trigger member for interaction with the canister and the switch, wherein when the triggering unit is mounted in the actuation housing and the canister moves from the rest position to the activation position the triggering member is configured such that after a predetermined displacement of the canister from the rest position into the intermediate position or into the activation position the canister interacts with the trigger member so that the trigger member triggers the switch when the canister reaches the intermediate position.

BRIEF DESCRIPTION OF THE FIGURES

The invention will now be described referring to an exemplary embodiment shown in the Figures in which.

Figure 1:
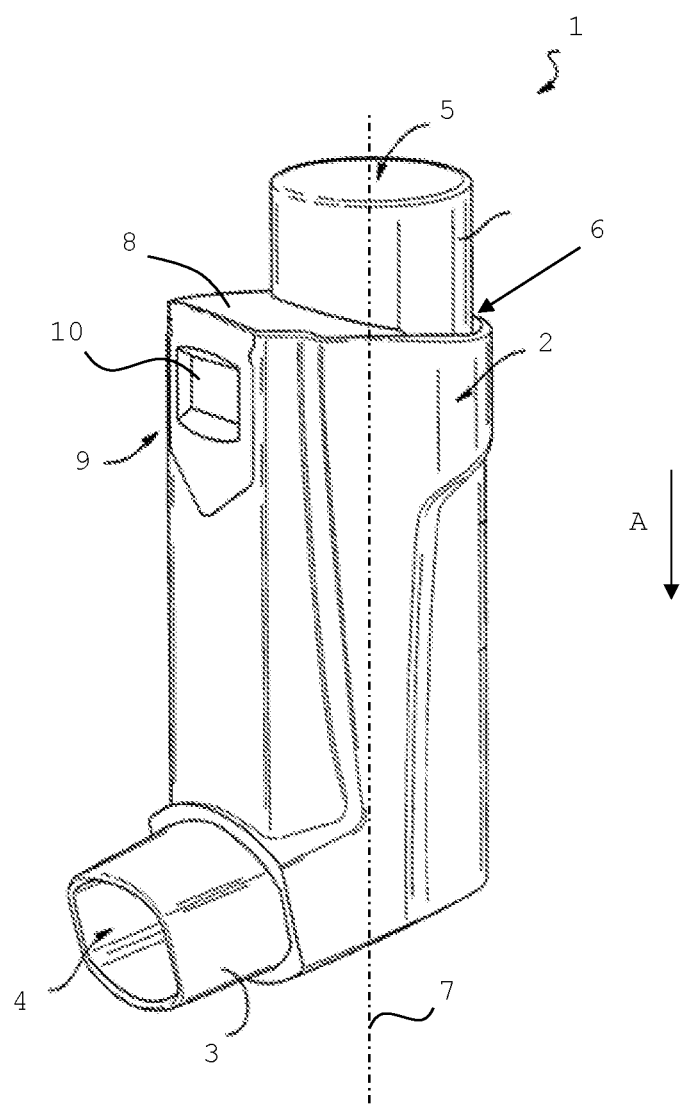
FIG. 1 shows a perspective view of a metered dose inhaler according to the present invention.

The metered dose inhaler (MDI) 1 for dispensing aerosol doses comprises an actuation housing 2 in the form of an L-shaped hollow body with two open ends. A dispensing end 3 at one leg of the L-shaped hollow body includes an opening 4 that constitutes a mouthpiece through which a patient inhales a pharmaceutical formulation contained in a canister 5. The canister 5 is received in a second end (receiving end 6) at the other leg of the L-shaped hollow body of the actuation housing 2. The dispensing end 3 communicates with the receiving end 6 via a through-going opening. The canister 5 is movable along a longitudinal axis 7 and is moved in the direction of the arrow A for initiating dispense of the aerosol.

The actuation housing 2 includes a triggering unit 8 that is inserted into the receiving end 6 of the actuation housing 2. Further, the actuation housing 2 has an opening 9 in its side wall through which a display 10 is visible.

Figure 2:
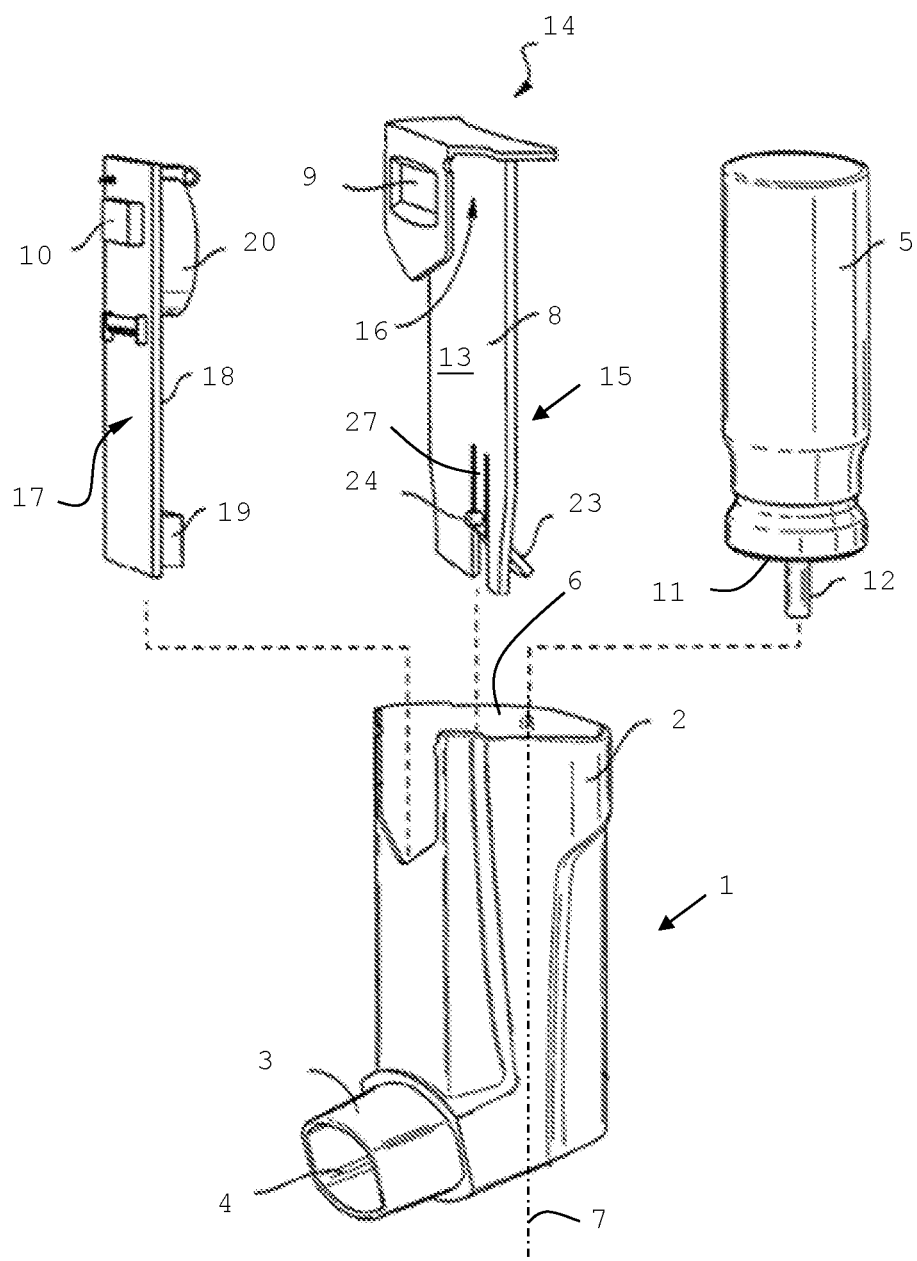
FIG. 2 shows a perspective exploded view of the metered dose inhaler of FIG. 1.

As shown in FIG. 2, the canister 5 comprises a valve 11 with a valve stem 12 positioned at a valve end thereof. The canister 5 is inserted into the receiving end 6 with the lower valve end. The triggering unit 8 includes an elongated body portion 13 in the form of a plate that extends substantially parallel to the longitudinal axis 7 of the actuation housing 2 when the triggering unit 8 is mounted in the actuation housing 2. The body portion 13 includes a top portion 14 and a bottom portion 15. The top portion 14 is formed as a cover for partially covering the actuation housing 2 (FIG. 1) and comprises a curved side face which is formed according to the outer measurements of the canister 5. The top portion 14 further includes an overhanging portion that forms an inverted U-shape defining a recess 16 that serves for accommodating a circuit assembly 17. The circuit assembly 17 includes a substrate 18 on which the display 10 is mounted. When the circuit assembly 17 is received in the recess 16 the display 10 is visible through the opening 9 of the actuation housing 2.

At the lower end of the circuit assembly 17, a switch 19 is mounted. The switch 19 is connected to a processing unit located on the substrate 18 and processing an electrical signal generated by the switch 19 when the switch 19 is triggered (pressed). A battery 20 is also mounted on the substrate 18.

The triggering unit 8 comprises a single trigger member 21 for triggering the electrical switch 19. The function of the trigger member 21 is provided by a single flexible tongue 22 which is integrally formed with the body portion 13 and which extends parallel to the body portion 13, wherein the lower end 23 of the flexible tongue is formed such as to project toward the canister 5 when mounted in the actuation housing 2, thereby giving the flexible tongue 22 a L-shaped appearance. The flexible tongue 22 can swivel toward the inner side and the other side of the actuation housing 2 (in lateral direction with respect to the longitudinal axis 7) in a flexible manner around its pivot point constituted by the connection to the body portion 13.

On the side of the flexible tongue 22 facing away from the canister 5, a knob 24 is formed. The knob 24 serves for pressing against the switch 19 when the flexible tongue 22 is bent outwardly.

Figure 3:
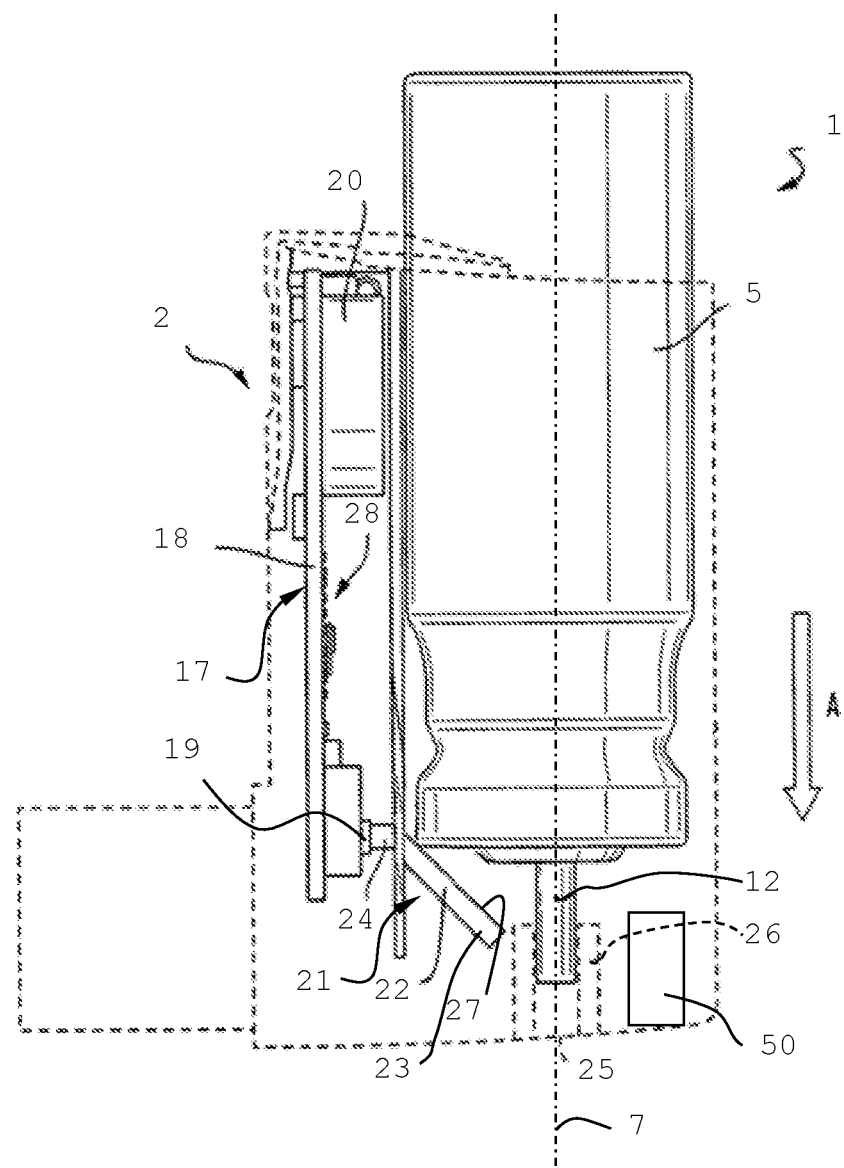
FIG. 3 shows internal parts of the metered dose inhaler of FIG. 1 in a side view in a first position.

FIG. 3 shows the components of the metered dose inhaler 1 mounted in the actuation housing 2. The canister 5 is movable along the longitudinal axis 7 but is shown in a rest position where the canister 5 has not been moved in the direction of the arrow A for administration of the medicinal product, yet. In this position, the valve end of the canister 5 does not bend the flexible tongue of the trigger member in outward direction. The knob 24 is arranged such as to face the switch 19 of the circuit assembly 17 without pressing the switch 19 in the rest position. The valve stem 12 is located above a lower contact surface or bottom surface 25 of the actuation housing 2 and is guided between guiding surfaces 26 of the actuation housing 2.

The lower end 23 of the trigger member 21 comprises an upper side 27 facing away from the bottom section of the actuation housing 2. The upper side 27 is adapted to form a contact surface for the canister 5, in particular the ferrule of the canister 5.

Figure 4:
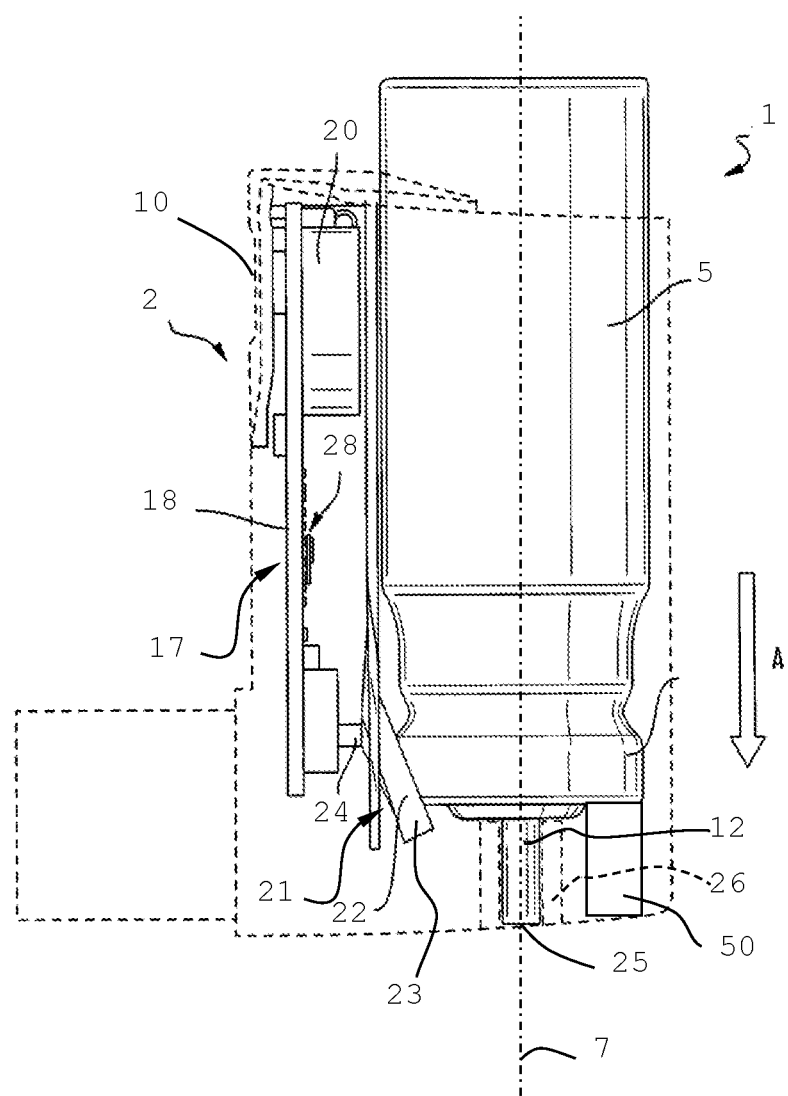
FIG. 4 shows internal parts of the metered dose inhaler of FIG. 1 in a side view in a second position.

FIG. 4 shows the metered dose inhaler 1 after displacement of the canister 5 in downward direction along the longitudinal axis 7 into an intermediate position which is located between the rest position and an actuation position in which the aerosol is dispensed. In this intermediate position, the valve stem 12 is in contact with the lower contact surface 25 of the actuation housing 2. However, the valve stem 12 has not been displaced relative to the canister body such as to open the valve, yet. Consequently, the valve 11 is not actuated and the aerosol is not dispensed.

The canister, however, has been displaced such as to engage the trigger member 21 and to tilt the trigger member 21 in outward direction. As a result, the trigger member 21, in particular the knob 24, has been moved laterally with respect to the longitudinal axis 7. The knob has engaged the switch 19 so that the switch 19 generates an electrical signal that is transmitted to the processing unit 28, when the canister 5 has reached the intermediate position. The processing unit 28 processes the electrical signal and displays proper information, such as a dose count value, on the display 10.

Further displacement of the canister 5 from the intermediate position in downward direction along the longitudinal axis 7 into an activation position opens the valve of the canister 5 as the valve stem 12 is displaced relative to the canister body. Consequently, the triggering unit 8 in connection with the circuit assembly 17 processes the triggering of the switch 19 prior to the actual opening of the valve 12. When the valve is being opened, the aerosol is released from the canister 5 and administered to the patient.

REFERENCE NUMERALS 1 metered dose inhaler
2 actuation housing
3 dispensing end of actuation housing
4 opening (mouthpiece)
5 canister 6 receiving end of actuation housing
7 longitudinal axis
8 triggering unit
9 opening in side wall
10 display
11 valve
12 valve stem
13 body portion of triggering unit
14 top portion of triggering unit
15 bottom portion of triggering unit
16 recess
17 circuit assembly
18 substrate of circuit assembly
19 switch
20 battery
21 trigger member
22 flexible tongue
23 lower end of flexible tongue
24 knob of flexible tongue
25 bottom portion/lower contact surface of housing
26 guidance
27 upper surface of flexible tongue
28 processing unit

The invention claimed is:

1. A metered dose inhaler for dispensing aerosol doses comprising:
   an actuation housing, and
   a canister containing an aerosol and having a valve located at a valve end thereof, wherein the canister is received in the actuation housing and is configured to move in a longitudinal direction from a rest position to an activation position in which the valve is depressed against a bottom portion of the actuation housing such that an aerosol dose is released,
   a triggering unit with a single trigger member formed by a flexible member, wherein the flexible member is configured to interact with the canister and to be moved by the canister in a lateral direction transverse to the longitudinal direction when the canister moves in the longitudinal direction from the rest position to the activation position,
   a circuit assembly having a substrate with a switch thereon, the switch being configured to interact with the trigger member such that the trigger member triggers the switch when the canister moves from the rest position to the activation position, wherein
   a) the flexible member is arranged such that after a predetermined displacement of the canister from the rest position into an intermediate position between the rest position and the activation position of the canister, the canister interacts with the flexible member so that the trigger member triggers the switch when the canister reaches the intermediate position, and wherein displacement from the intermediate position to the actuation position causes displacement of the valve so that the aerosol dose is released, or wherein
   b) the flexible member is arranged such that the trigger member triggers the switch when the canister reaches the activation position,
   wherein the triggering unit comprises a body portion that is positioned in the actuation housing between a wall of the actuation housing and the canister, wherein the circuit assembly is attached to the body portion and the flexible member is attached to the body portion and extends in the longitudinal direction so that the trigger member is resiliently pivotable in the lateral direction with respect to the body portion, and the body portion comprises a plate that extends in the longitudinal direction.

2. The metered dose inhaler of claim 1, wherein the metered dose inhaler further comprises a mechanical dose counter that is arranged to be triggered by the canister when or before the canister reaches the activation position.

3. The metered dose inhaler of claim 2, wherein in the intermediate position of the canister further displacement of the canister toward the activation position triggers opening of the valve.

4. The metered dose inhaler of claim 1, wherein in the intermediate position of the canister further displacement of the canister toward the activation position triggers opening of the valve.

5. The metered dose inhaler of claim 1, wherein the actuation housing is adapted such that in the intermediate position the valve of the canister is depressed but closed.

6. The metered dose inhaler of claim 1, wherein in the intermediate position, the valve of the canister rests against the bottom surface of the actuation housing.

7. The metered dose inhaler of claim 1, wherein the flexible member is formed as a flexible tongue that extends from the body portion of the triggering unit in longitudinal direction, wherein at least a part of the flexible tongue extends toward the canister.

8. The metered dose inhaler of claim 7, wherein the flexible member is primarily tilted in the lateral direction with respect to the body portion when the flexible member is engaged by the canister.

9. The metered dose inhaler of claim 1, wherein the flexible member is primarily tilted in the lateral direction with respect to the body portion when the flexible member is engaged by the canister.

10. The metered dose inhaler of claim 1, wherein the actuation housing has an L-shaped hollow body with a dispensing end at one end of the actuation housing and a receiving end at the other end of the actuation housing, wherein the body portion of the triggering unit is mounted in the actuation housing by being inserted into the receiving end.

11. The metered dose inhaler of claim 1, wherein the circuit assembly includes a counting circuit configured to determine the time when the switch is triggered by the trigger member.

12. The metered dose inhaler of claim 1, wherein the switch is part of an electrical dose counter.

13. The metered dose inhaler of claim 1, comprising a display operatively connected to the circuit assembly and configured to display information processed by the circuit assembly and/or wherein the circuit assembly is configured to activate sensors from a sleep mode upon activation of the switch.

14. A triggering unit for a metered dose inhaler having one single trigger member thereon, the triggering unit being configured to interact with a canister of the metered dose inhaler when the canister moves in a longitudinal direction from a rest position to an activation position;
   wherein the trigger member is positioned to activate a switch when the canister moves in the longitudinal direction and is formed by a flexible member;
   wherein the triggering unit comprises a body portion that is configured to be positioned in an actuation housing of the metered dose inhaler between a wall of the actuation housing and the canister, and
   wherein the body portion comprises a plate that extends in the longitudinal direction, and wherein the flexible member is attached to the body portion and extends in the longitudinal direction so that the trigger member is resiliently pivotable in the lateral direction with respect to the body portion.

15. The triggering unit of claim 14 which comprises one flexible tongue that is operatively connected to the trigger member, wherein the flexible tongue is configured to move the trigger member in a lateral direction transverse to the longitudinal direction when the canister reaches the intermediate position or the activation position.

* * * * *